(12) United States Patent
Morris et al.

(10) Patent No.: US 8,123,892 B2
(45) Date of Patent: Feb. 28, 2012

(54) UROLOGY CATHETER

(75) Inventors: Robert A Morris, Milton, MA (US); Rita Ann Morris, legal representative, Milton, MA (US); Cliff Karl, Buzzards Bay, MA (US); Kurt Green, Wrentham, MA (US); Tony Sacchetti, Quincy, MA (US); Chris Dubeau, Attleboro, MA (US); Stephen Murray, North Attleboro, MA (US); James A Walls, Dunwoody, GA (US)

(73) Assignee: Tyco Healthcare Group LP, Mansfield, MA (US)

( * ) Notice: Subject to any disclaimer, the term of this patent is extended or adjusted under 35 U.S.C. 154(b) by 256 days.

(21) Appl. No.: 12/636,170

(22) Filed: Dec. 11, 2009

(65) Prior Publication Data

US 2010/0089528 A1   Apr. 15, 2010

Related U.S. Application Data

(62) Division of application No. 10/951,178, filed on Sep. 27, 2004, now Pat. No. 7,655,000.

(60) Provisional application No. 60/506,403, filed on Sep. 26, 2003.

(51) Int. Cl.
*B29C 47/00* (2006.01)
*A61M 31/00* (2006.01)
*A61M 37/00* (2006.01)

(52) U.S. Cl. ..................... 156/245; 604/93.01; 604/540

(58) Field of Classification Search ............... 604/96.01, 604/102.2, 103.02, 103.06–103.09, 540–544; 156/155, 242, 245, 247
See application file for complete search history.

(56) References Cited

U.S. PATENT DOCUMENTS 3,547,126 A   12/1970   Birtwell
(Continued)

FOREIGN PATENT DOCUMENTS

EP   1116567 A2 *   7/2001
(Continued)

OTHER PUBLICATIONS

English translation of JP 11-276594 to Kawakita et al.*

*Primary Examiner* — Melanie Hand
(74) *Attorney, Agent, or Firm* — Lisa E. Winsor, Esq.

(57) ABSTRACT

A urology catheter is provided that includes an elongated body extending from a proximal end to a distal end. The body defines at least one lumen. A tip has a proximal end that is disposed in abutting relation with the distal end of the body such that the body is fixed with the tip. The tip defines a lateral opening that is defined by a wall including an external radius disposed in transition with an outer surface of the tip and an internal radius disposed in transition with an inner surface of the tip. The external radius has a non-perpendicular profile with the outer surface of the tip. An expandable member has a proximal portion disposed about the body and a distal portion disposed about the tip. A method of manufacturing the urology catheter is provided.

8 Claims, 13 Drawing Sheets

U.S. PATENT DOCUMENTS

| | | | |
|---|---|---|---|
| 3,832,253 A | 8/1974 | DiPalma et al. |
| 3,865,666 A | 2/1975 | Shoney |
| 3,890,976 A | 6/1975 | Bazell et al. |
| 3,926,705 A | 12/1975 | Todd |
| 4,018,231 A | 4/1977 | Wallace |
| 4,207,900 A | 6/1980 | Patel et al. |
| 4,210,478 A | 7/1980 | Shoney |
| 4,222,384 A | 9/1980 | Birtwell |
| 4,284,459 A | 8/1981 | Patel et al. |
| 4,292,270 A | 9/1981 | Hannah et al. |
| 4,361,152 A | 11/1982 | Patel |
| 4,437,856 A | 3/1984 | Valli |
| 4,447,228 A | 5/1984 | Patel |
| 4,555,242 A | 11/1985 | Saudagar |
| 4,575,371 A | 3/1986 | Nordqvist et al. |
| 4,777,951 A | 10/1988 | Cribier et al. |
| 4,850,969 A | 7/1989 | Jackson |
| 4,878,495 A | 11/1989 | Grayzel |
| 5,032,113 A | 7/1991 | Burns |
| 5,192,296 A | 3/1993 | Bhate et al. |
| 5,195,507 A | 3/1993 | Bilweis |
| 5,195,970 A | 3/1993 | Gahara |
| 5,250,070 A | 10/1993 | Parodi |
| 5,254,089 A | 10/1993 | Wang |
| 5,328,469 A | 7/1994 | Coletti |
| 5,342,301 A | 8/1994 | Saab |
| 5,364,357 A | 11/1994 | Aase |
| 5,403,280 A | 4/1995 | Wang |
| 5,456,666 A | 10/1995 | Campbell |
| 5,458,572 A | 10/1995 | Campbell et al. |
| 5,470,313 A | 11/1995 | Crocker et al. |
| 5,476,477 A | 12/1995 | Burns |
| 5,478,319 A | 12/1995 | Campbell et al. |
| 5,527,281 A | 6/1996 | Haas |
| 5,645,528 A | 7/1997 | Thome |
| 2004/0087902 A1 | 5/2004 | Richter |

FOREIGN PATENT DOCUMENTS

| | | | |
|---|---|---|---|
| JP | 11276594 A | 10/1999 |

\* cited by examiner

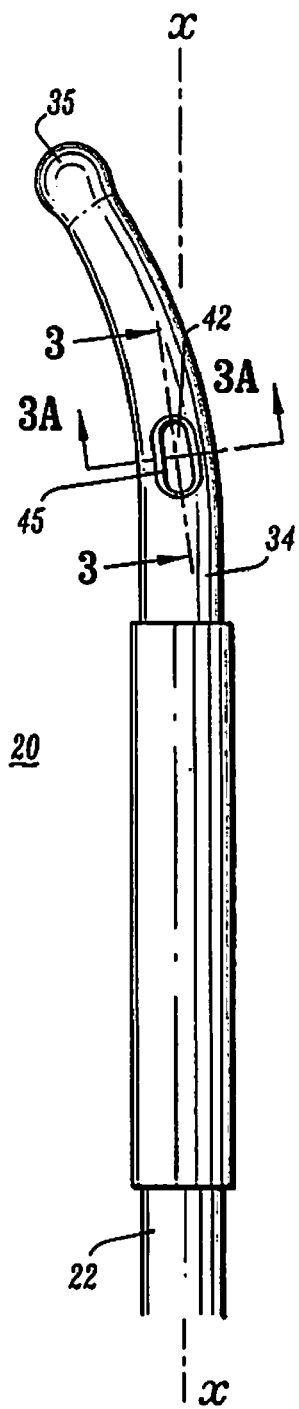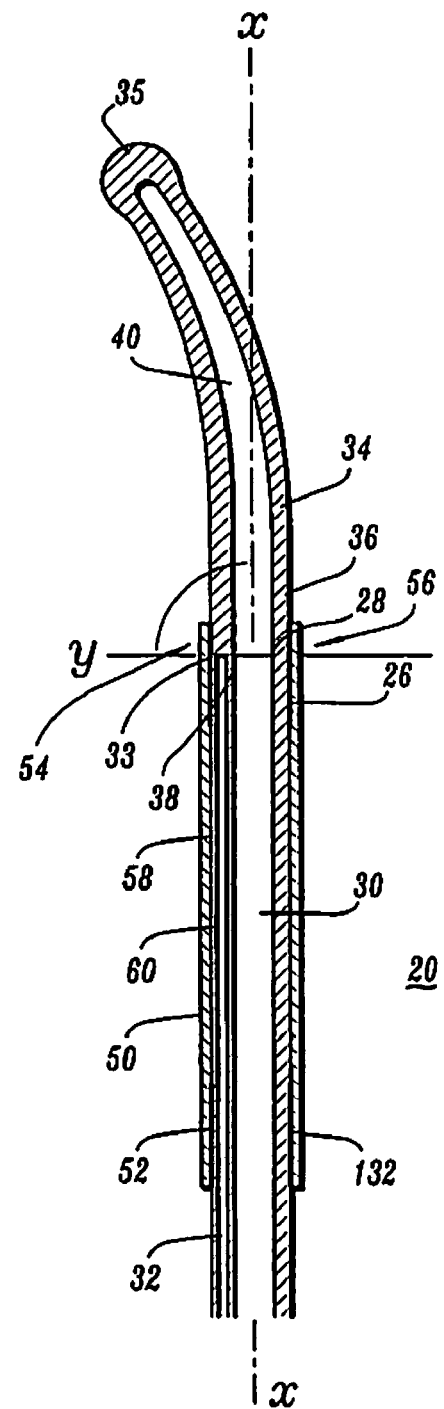
FIG. 1   FIG. 2

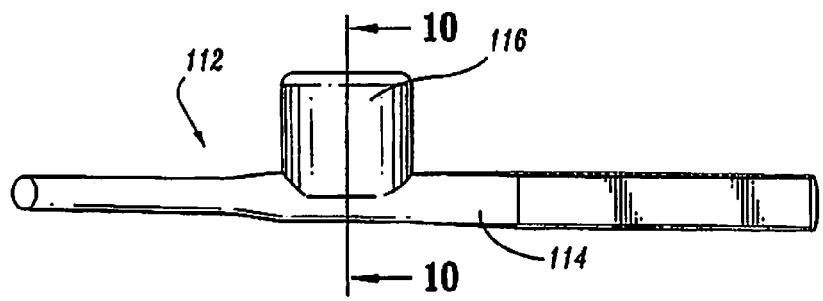
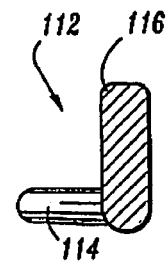
FIG. 9
FIG. 10
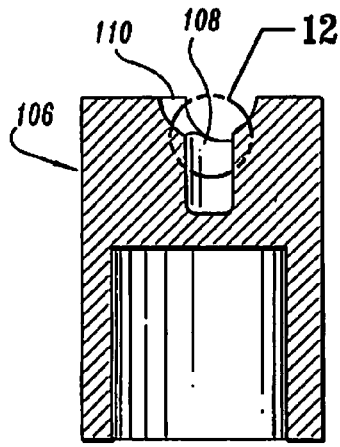
FIG. 11
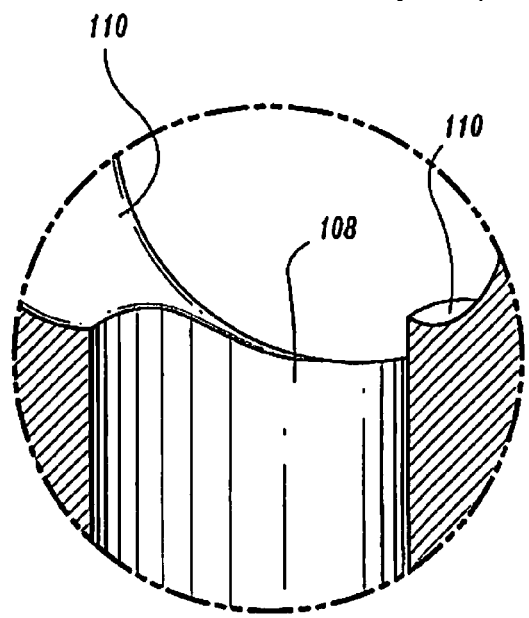
FIG. 12
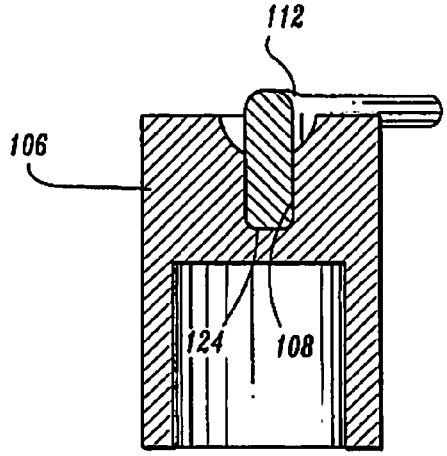
FIG. 13

UROLOGY CATHETER

CROSS-REFERENCE TO RELATED APPLICATIONS

This application is a divisional application of U.S. patent application Ser. No. 10/951,178, filed Sep. 27, 2004, which application claims priority to U.S. Provisional Patent Application Ser. No. 60/506,403, filed Sep. 26, 2003, the entire contents of these applications being hereby incorporated herein by reference.

BACKGROUND

1. Technical Field

The present disclosure relates generally to medical catheters, and more particularly to a urology catheter including an advantageous tip configuration and related method of manufacture.

2. Description of the Related Art

As is known, urinary catheters may be employed to transport urine collected in the bladder out of a patient via the urinary tract. For example, urinary catheters such as Foley catheters have a shaft including a drainage lumen that communicates with drainage eyes disposed adjacent a distal end thereof. An inflatable balloon is disposed adjacent the distal end of the shaft. During placement, the distal end of the shaft is passed through the patient's urethra until the balloon and drainage eyes are located in the patient's bladder. The balloon is inflated through an inflation lumen to retain the catheter in the bladder. Urine may drain through the drainage eyes and drainage lumen, which is in communication with a proximal end of the catheter. The proximal end of the catheter is connected to a receptacle for collection of urine.

Various known urology catheters may be produced with a liquid injection molded tip that is attached to the catheter shaft. Typically, the drain eyes of the urinary catheter are formed via a punching operation. This punching operation, however, can disadvantageously result in jagged edges around the eyes and an inconsistent eye size. Other known urinary catheters may include molded drain eyes.

These known manufacturing apparatus and techniques suffer from various drawbacks. For example, the size of the drain eye may be limited disadvantageously resulting in inferior drainage or rapid blockage due to encrustation. Alternatively, due to manufacturing constraints, the size of the drain eye may have to be increased to accommodate the manufacturing apparatus. An increase in size of the drain eye may cause the tip to become undesirably flexible, disadvantageously resulting in difficult insertion with the body due to tip deflection.

Therefore, it would be desirable to have a urology catheter including an advantageous tip configuration and related method of manufacture that improves drainage characteristics, avoids encrustation and enhances stiffness to facilitate tip insertion with a patient. Desirably, a drain eye of the urology catheter is defined by an external radius and an internal radius of the tip. It would be highly desirable if the urology catheter and its constituent parts are easily and efficiently manufactured and assembled.

SUMMARY

Accordingly, a urology catheter is provided that includes an advantageous tip configuration and related method of manufacture that improves drainage characteristics, avoids encrustation and enhances stiffness to facilitate tip insertion with a patient to overcome the discussed disadvantages and drawbacks of the prior art. Desirably, the urology catheter includes a drain eye that is defined by an external radius and an internal radius of the tip. Most desirably, the urology catheter is easily and efficiently manufactured and assembled.

In one particular embodiment, a urology catheter is provided, in accordance with the principles of the present disclosure. The catheter includes an elongated body extending from a proximal end to a distal end. The body defines at least one lumen. A tip has a proximal end that is disposed in abutting relation with the distal end of the body such that the body is fixed with the tip. The tip defines a lateral opening that is defined by a wall including an external radius disposed in transition with an outer surface of the tip and an internal radius disposed in transition with an inner surface of the tip. The external radius has a non-perpendicular profile with the outer surface of the tip. An expandable member has a proximal portion disposed about the body and a distal portion disposed about the tip. The lateral opening may be formed by a molding process. The tip and the body may be fabricated from a material including silicone.

Alternatively, the body can define a first lumen and a second lumen configured for fluid flow to inflate the expandable member. In an alternate embodiment, an expansion device is disposed within the body adjacent to the expandable member.

In another alternate embodiment, the catheter includes a body defining a longitudinal axis and having a distal end. A tip having a proximal end is disposed in abutting relation with the distal end of the body such that the body is fixed with the tip. An expandable member having a proximal securing portion is disposed about the body. A distal securing portion is disposed about the body and the tip. The distal securing portion of the expandable member is bonded over an abutment region of the body and the tip. The distal securing portion of the expandable member can be adhesively bonded over a region of fixation between the body and the tip.

In another alternate embodiment, the catheter includes an elongated body defining a longitudinal axis and extending from a proximal end to a distal end. The distal end defines a planar face that has a substantially perpendicular orientation relative to the longitudinal axis. The body further defines a first lumen and a second lumen. A tip having a proximal end defines a planar face. The planar face of the tip is disposed in abutting relation with the planar face of the body such that the body is secured with the tip. The tip further defines a central lumen that is in fluid communication with the first lumen. The tip has a lateral opening that is defined by a wall having a radius of curvature. The radius of curvature includes an external radius disposed in transition with an outer surface of the tip and an internal radius disposed in transition with an inner surface of the tip. A cuff having a proximal securing portion is disposed about the body and a distal securing portion is disposed about the tip. The distal securing portion of the cuff is bonded over an abutment region of the body and the tip. The cuff defines an inflation cavity with an outer surface of the body that is in fluid communication with the second lumen. A cross sectional area of the central lumen may be greater than a cross sectional area of the first lumen.

In another particular embodiment, a method of manufacturing a catheter having a body and a tip is provided, in accordance with the principles of the present disclosure. The method includes the steps of providing a mold that defines a mold cavity and a post cavity that communicates with the mold cavity, the post cavity defines a predetermined transition configuration; providing a pin having a post extending therefrom, the post cooperating with the predetermined transition configuration of the post cavity to form the tip; inserting the pin with a distal end of the body; disposing the distal end of the body and the pin into the mold cavity such that the post is disposed with the post cavity and, the post cavity defining a non-perpendicular transition configuration extending to engage a wall of the post cavity; injecting a material into the mold cavity to simultaneously mold the tip with the distal end of the body, and to mold a lateral opening with the tip in relation to the predetermined transition configuration such that the lateral opening is defined by a wall including an external radius disposed in transition with an outer surface of the tip and an internal radius disposed in transition with an inner surface of the tip, the external radius having a non-perpendicular profile with the outer surface of the tip; removing the body and the pin from the mold cavity; and removing the pin from the catheter through the lateral opening. Alternatively, the method may include the step of mounting an expandable member about the body and the tip.

In alternate embodiment, the method includes the steps of providing a mold assembly that includes a mold cavity, the mold assembly having a removable spring block that forms a portion of the mold cavity and defines a post cavity that communicates with the mold cavity, the post cavity defining a non-perpendicular transition configuration; providing a pin having a core and a post extending therefrom, the post cooperating with the non-perpendicular transition configuration to form the tip; inserting the core with a distal end of the body; disposing the distal end of the body and the pin with the mold cavity such that the core is spaced apart from walls of the mold cavity and the post is disposed with the post cavity and extends to engage a wall of the post cavity; injecting a silicone based material into the mold cavity to simultaneously mold the tip with the distal end of the body such that the tip defines a central lumen, and to mold a lateral opening with the tip in relation to the non-perpendicular transition such that the lateral opening is defined by a wall including an external radius disposed in transition with an outer surface of the tip and an internal radius disposed in transition with an inner surface of the tip, the external radius having a non-perpendicular profile with the outer surface of the tip and the internal radius having a non-perpendicular profile with the inner surface of the tip; removing the body and the spring block, having the pin disposed therewith, from the mold cavity; removing the pin from the tip through the lateral opening; and mounting an expandable sleeve about the body and the tip.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages, may be best understood by reference to the following description, taken in connection with the accompanying drawings, as set forth below.

FIG. 1 is a plan view of a distal portion of the urology catheter in accordance with the principles of the present disclosure;

FIG. 2 is a cross-sectional view of the urology catheter shown in FIG. 1;

FIG. 9 is a side view of the pin shown in FIG. 6;

FIG. 10 is an alternate side cross-sectional view taken along lines 10-10 shown in FIG. 9 of the pin, in part elevation;

FIG. 11 is a side cross-sectional view of a spring block shown in FIG. 6;

FIG. 12 is a side cross-sectional view of the indicated area of detail shown in FIG. 11;

FIG. 13 is a side cross-sectional view of the spring block assembly shown in FIG. 6, illustrating the pin in part elevation;

DETAILED DESCRIPTION OF THE EXEMPLARY EMBODIMENTS

Figure 3:
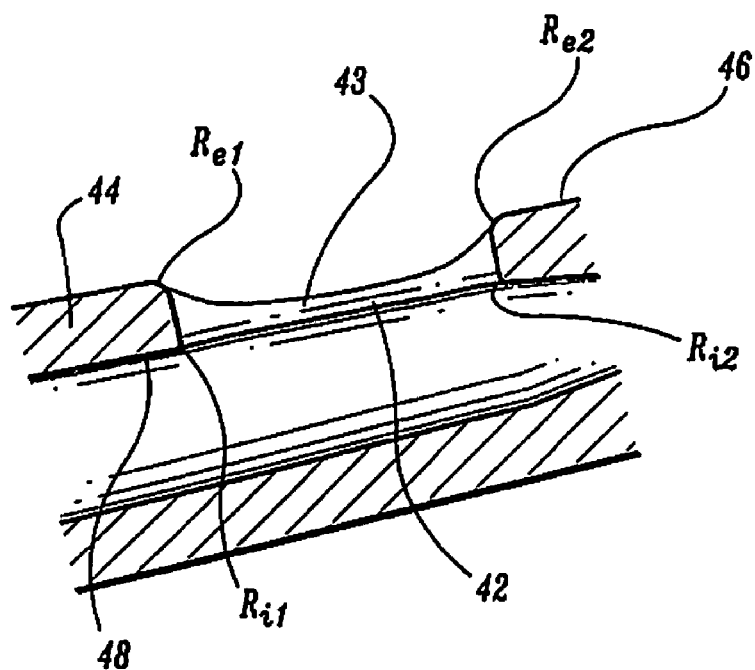
FIG. 3 is a cutaway cross-sectional view of the urology catheter taken along lines 3-3 shown in FIG. 1.

The exemplary embodiments of the urology catheter and methods of use disclosed are discussed in terms of medical catheters for the administration of fluids (withdrawal, introduction, and other procedures) with the body of a subject and more particularly, in terms of a urology catheter including an advantageous tip configuration and related method of manufacture that improves drainage characteristics and enhances stiffness to facilitate tip insertion with a patient. The urology catheter can include molded openings, tip and shaft members that may be fabricated from a variety of different materials having varying durometer and flexibility characteristics. It is contemplated that the catheter can be used for various applications for the administration of fluids such as, for example, surgical, diagnostic and related treatments of diseases, and body ailments of a subject. It is further contemplated that the principles relating to the catheter disclosed include employment with various catheter related procedures, such as, for example, abdominal, urinary and intestinal applications. It is envisioned that the catheter can be used for administration of fluids such as, for example, the introduction of medication and saline, and withdrawal of fluids such as, blood, urine, and other bodily fluids.

In the discussion that follows, the term "proximal" will refer to the portion of a structure that is closer to a practitioner, while the term "distal" will refer to the portion that is further from the practitioner. As used herein, the term "subject" refers to a human patient or other animal. According to the present disclosure, the term "practitioner" refers to a doctor, nurse or other care provider and may include support personnel.

The following discussion includes a description of a urology catheter, in accordance with the principles of the present disclosure. Reference will now be made in detail to the exemplary embodiments of the disclosure, which are illustrated in the accompanying figures.

Turning now to the figures, wherein like components are designated by like reference numerals throughout the several views. Referring initially to FIGS. 1-5, a urology catheter 20 includes an elongated body 22 defining a longitudinal axis x. Body 22 is tubular and extends from a proximal end (not shown) to a distal end 26. It is contemplated that body 22 may be variously dimensioned and attachable to other medical devices. For example, catheter 20 may be variously sized such as 12, 16, 18 and 26 French. It is further contemplated that the outer surface of body 22 may have various configurations, such as, for example, rectangular, elliptical, polygonal, etc.

Distal end 26 defines a planar face 28 that has a substantially perpendicular orientation relative to longitudinal axis x. Planar face 28 is disposed along a plane y for attachment with a tip, as will be discussed. It is envisioned that planar face 28 may alternatively be disposed in various angular orientations relative to longitudinal axis x, such as acute and obtuse.

Body 22 defines a first lumen, such as, for example, drainage lumen 30 and a second lumen, such as, for example, inflation lumen 32. Drainage lumen 30 is configured for fluid flow and in communication with the proximal end of catheter 20 for drainage of urine from a bladder of a subject (not shown). The proximal end of catheter 20 is connected to a receptacle (not shown) for collection of the urine.

Inflation lumen 32 is configured for fluid and/or gas flow to inflate an expandable member, as will be discussed. Inflation lumen 32 is disposed adjacent distal end 26 of body 22 and includes a port 33 for fluid connection with the expandable member. Lumens 30, 32 may be uniformly dimensioned or include alternative dimensional cross sections within body 22, such as, narrow and broad portions, converging surfaces, undulating surfaces, etc. according to the particular flow indications and/or flow rate requirements. It is contemplated lumens 30, 32 may extend uniform or alternative lengths. It is further contemplated that body 22 may include one or a plurality of lumens.

A flexible tubular tip 34 is configured for insertion with the urethra of a subject and disposal within the bladder. Tip 34 has a flexible curved body and a cylindrical head 35. Tip 34 has a proximal end 36 that defines a planar face 38. Planar face 38 of tip 34 is disposed in abutting relation with planar face 28 of body 22 such that body 22 is secured with tip 34. Planar face 38 has a substantially perpendicular orientation relative to longitudinal axis x, Planar face 38 is disposed along plane y for attachment with planar face 28 of body 22, as will be discussed. It is envisioned that planar face 38 may alternatively be disposed in various angular orientations relative to longitudinal axis x, such as acute and obtuse. It is contemplated that tip 34 may be uniformly aligned with longitudinal axis x or alternatively have varying degrees of curvature. It is further contemplated that tip 34 may be employed with a guide wire or stylet. Head 35 may have alternative geometric configurations according to the requirements of a particular application.

Tip 34 defines a central lumen 40 that is in fluid communication with drainage lumen 30 for drainage of urine from the bladder. Tip 34 has a lateral opening, such as, for example, drain eye 42 that communicates with central lumen 40 and is configured for disposal within the bladder for urine drainage.

Figure 3A:
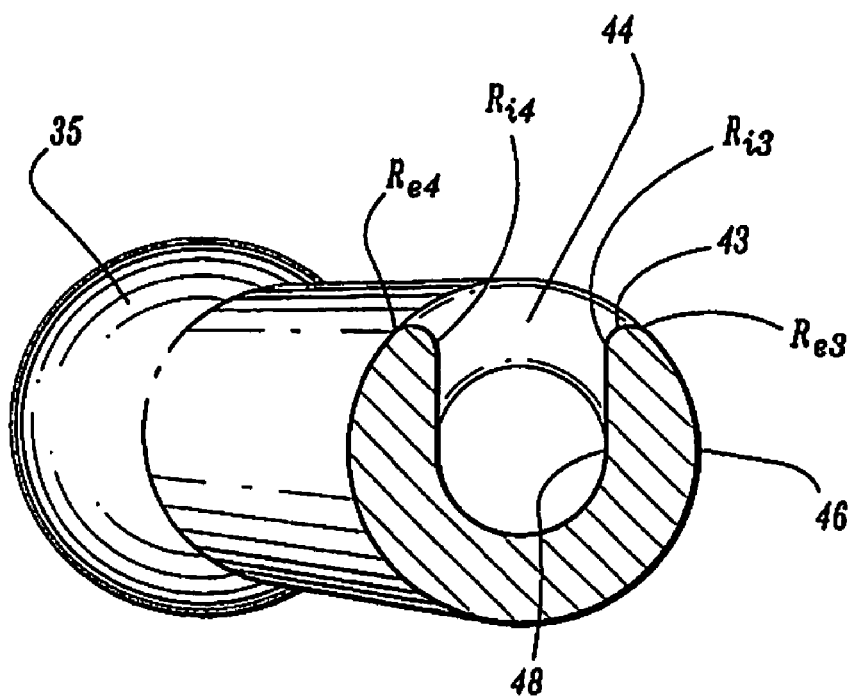
FIG. 3A is a cutaway perspective view of the urology catheter taken along lines 3A-3A shown in FIG. 1.
Figure 3B:
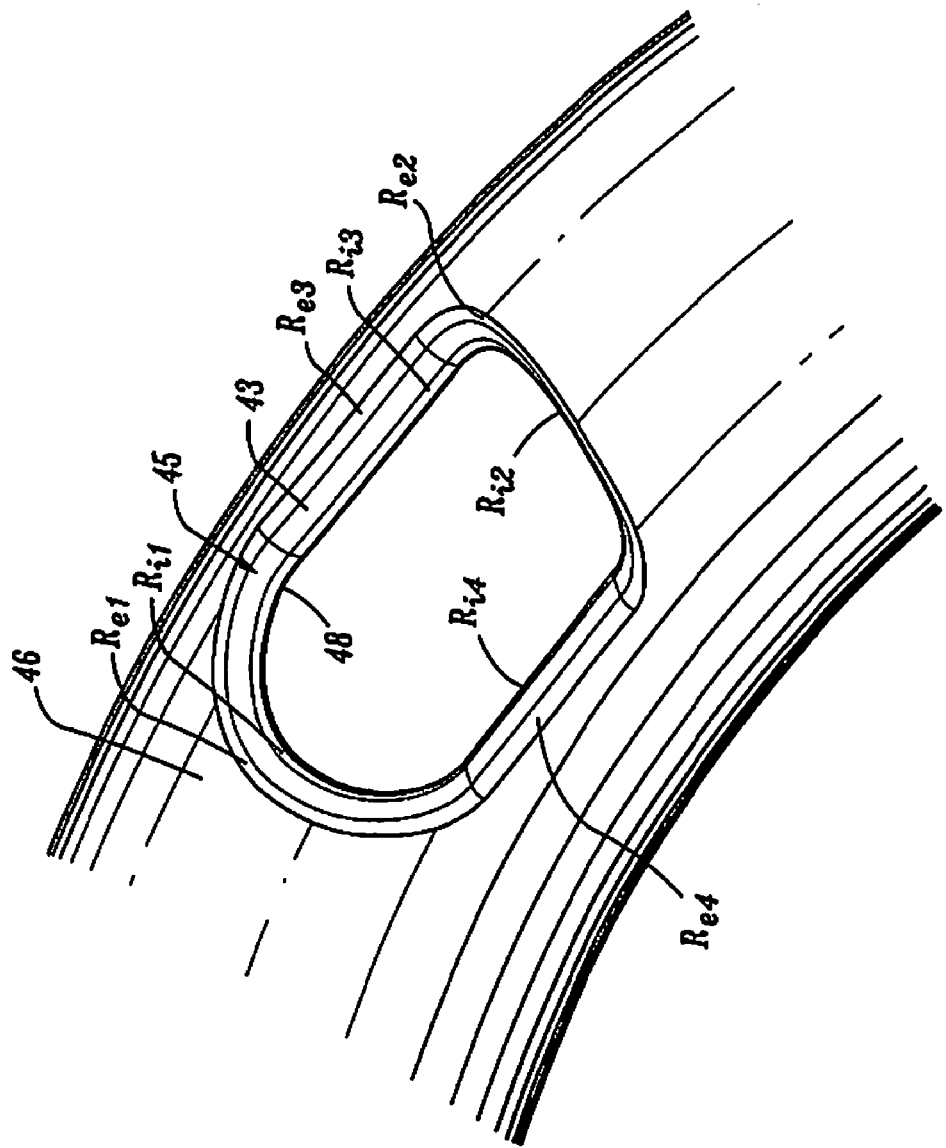
FIG. 3B is a cutaway perspective view of a lateral opening of the urology catheter shown in FIG. 1.
Figure 4:
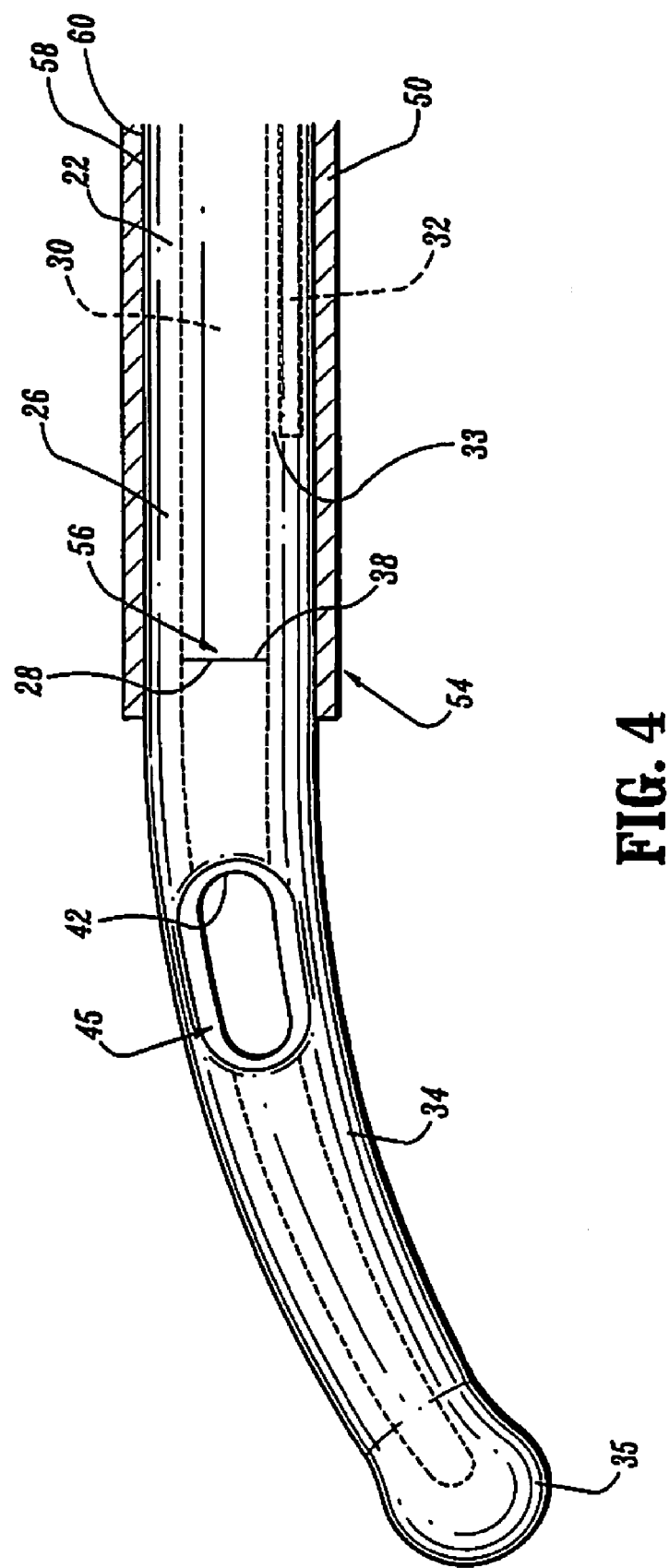
FIG. 4 is a cutaway side view of the urology catheter shown in FIG. 1, illustrating lumens in phantom.
Figure 5:
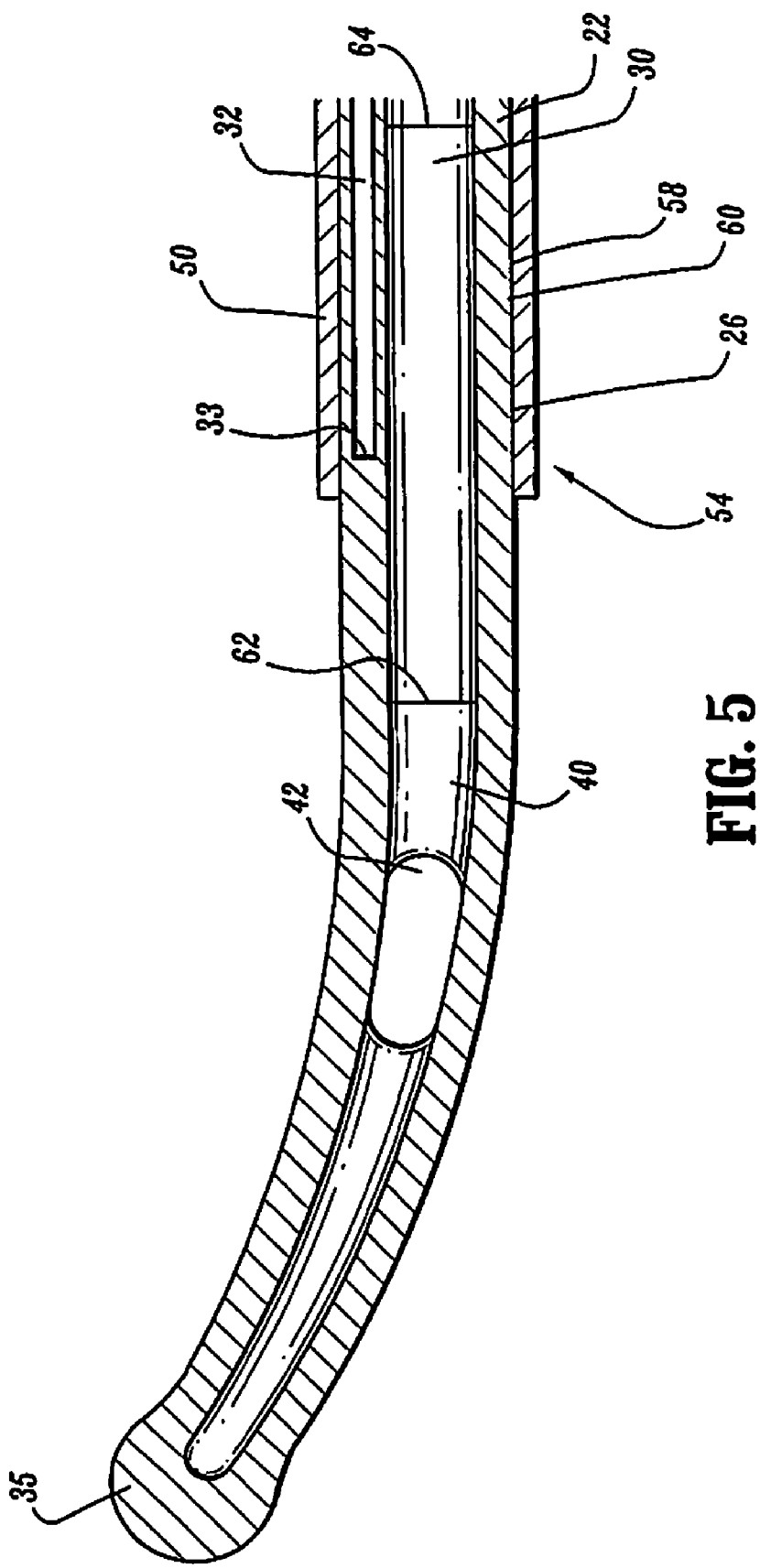
FIG. 5 is a cutaway cross-sectional side view of the urology catheter shown in FIG. 1.
Figure 6:
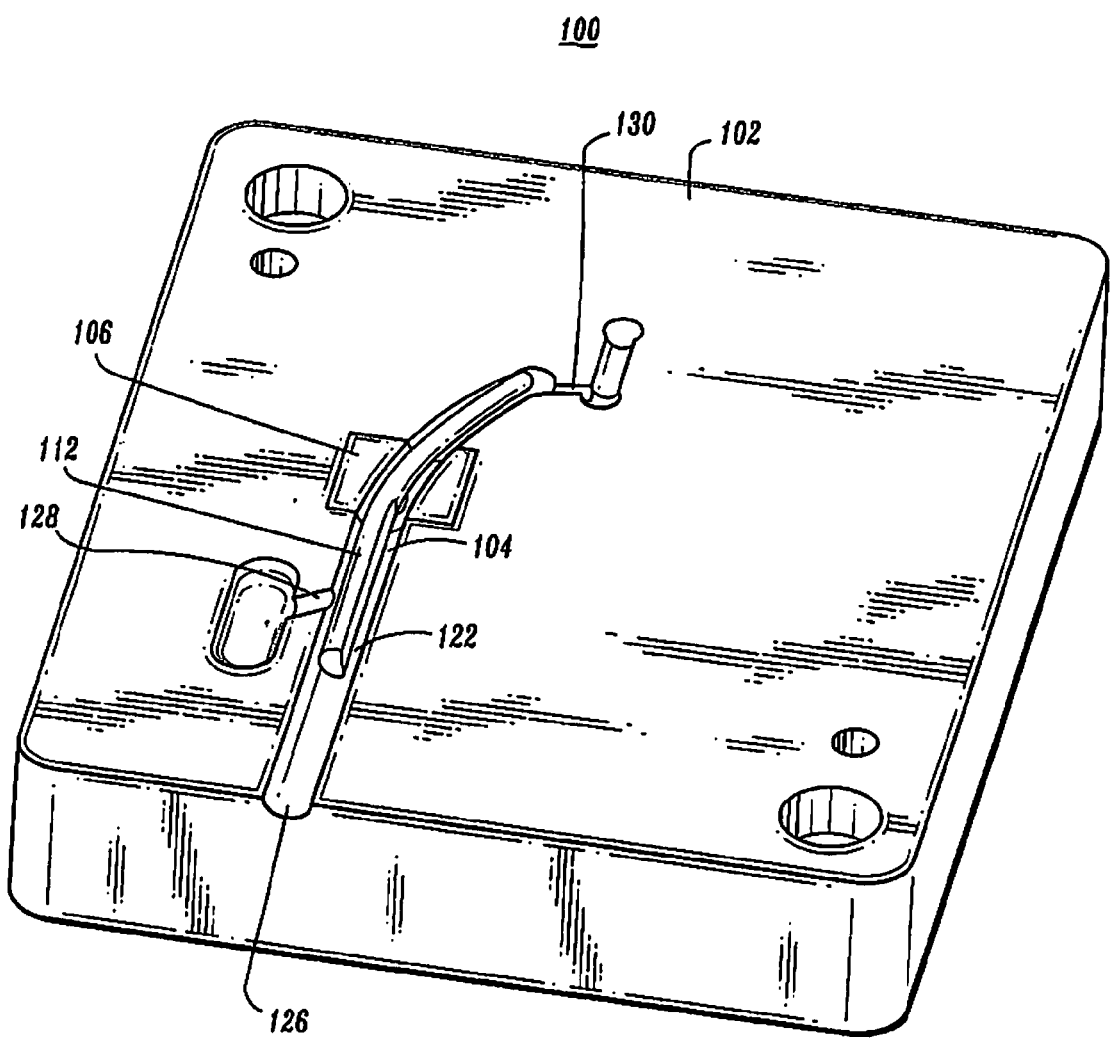
FIG. 6 is a perspective view of a mold assembly, with a section removed, in accordance with the principles of the present disclosure.

Referring to FIGS. 3, 3A and 3B, drain eye 42 is defined in a wall 44 of tip 34. The opening of drain eye 42 is defined by a surface 45 that is disposed about the perimeter of drain eye 42. Surface 45 has a radius of curvature R about the perimeter of drain eye 42. Radius of curvature R includes an external radii and an internal radii relative to wall 44, with a chamfer surface 43 disposed therebetween. Chamfer 43 may be variously dimensioned and oriented, such as, for example, 0.010 inch thickness by 45 degree inclination relative to a plane defined by wall 44, 0.030 inch thickness by 30 degree inclination, 0.015 inch thickness by 45 degree inclination, 0.025 inch thickness by 55 degree inclination as well as other dimensions and orientations according to the requirements of a particular application.

Radius of curvature R includes an external radii $R_{e1}$ and $R_{e2}$, which are disposed in transition with an outer surface 46 of tip 34. Radius $R_{e1}$ is disposed adjacent a distal end of drain eye 42 and $R_{e2}$ is disposed adjacent a proximal end of drain eye 42. External radii $R_{e1}$ and $R_{e2}$ have a non-perpendicular profile with outer surface 46. External radii $R_{e1}$ and $R_{e2}$ may uniformly or alternatively be perpendicularly disposed, non-perpendicularly disposed or disposed at various radial orientations relative to outer surface 46 of tip 34. External radii $R_{e1}$ and $R_{e2}$ may be variously dimensioned, such as, for example, in the range of 0.005-0.080 inch radius as well as other dimensions according to the requirements of a particular application.

Radius of curvature R also includes an internal radii $Ri_1$ and $Ri_2$, which are disposed in transition with an inner surface 48 of tip 34. Radius $Ri_1$ is disposed adjacent a distal end of drain eye 42 and $Ri_2$ is disposed adjacent a proximal end of drain eye 42. Internal radii $Ri_1$ and $Ri_2$ are disposed in a substantially perpendicular profile with inner surface 48. Internal radii $Ri_1$ and $Ri_2$ may uniformly or alternatively be perpendicularly disposed, non-perpendicularly disposed or disposed at various radial orientations relative to inner surface 48 of tip 34. Internal radii $Ri_1$ and $Ri_2$ may be variously dimensioned, such as, for example, in the range of 0.005-0.080 inch radius as well as other dimensions according to the requirements of a particular application.

Radius of curvature R also includes an external radii $R_{e3}$ and $R_{e4}$, which are disposed in transition with outer surface 46 of tip 34. External radii $R_{e3}$ and $R_{e4}$ are disposed adjacent side portions of drain eye 42. External radii $R_{e3}$ and $R_{e4}$ have a non-perpendicular profile with outer surface 46. External radii $R_{e3}$ and $R_{e4}$ may uniformly or alternatively be perpendicularly disposed, non-perpendicularly disposed or disposed at various radial orientations relative to outer surface 46 of tip 34. External radii $R_{e3}$ and $R_{e4}$ may be variously dimensioned, such as, for example, in the range of 0.005-0.080 inch radius as well as other dimensions according to the requirements of a particular application.

Radius of curvature R also includes an internal radii $R_{i3}$ and $R_{i4}$, which are disposed in transition with inner surface 48 of tip 34. Internal radii $R_{i3}$ and $R_{i4}$ are disposed adjacent side portions of drain eye 42. Internal radii $R_{i3}$ and $R_{i4}$ have a non-perpendicular profile with inner surface 48. Internal radii $R_{i3}$ and $R_{i4}$ may uniformly or alternatively be perpendicularly disposed, non-perpendicularly disposed or disposed at various radial orientations relative to inner surface 48 of tip 34. Internal radii $R_{i3}$ and $R_{i4}$ may be variously dimensioned, such as, for example, in the range of 0.005-0.080 inch radius as well as other dimensions according to the requirements of a particular application.

This configuration of drain eye 42 advantageously improves drainage characteristics of catheter 20, avoids encrustation during use and enhances stiffness to facilitate tip 34 insertion with a subject. Drain eye 42 optimizes central lumen 40 area to improve fluid flow. The geometry of drain eye 42, including the radii and chamfer discussed, provides a smooth transition about its perimeter, which facilitates a laminar flow of fluids exiting drain eye 42. The laminar flow prevents bacteria buildup and the formation of a bacteria film or the like about drain eye 42.

Tip 34 has enhanced stiffness to facilitate manipulation due to the improved flow characteristics of drain eye 42, which avoids the necessity for an oversized drain eye. Accordingly, the wall thickness of tip 34 can be optimized for stiffness. It is contemplated that the stiffness of tip 34 may be further enhanced by material selection. It is envisioned that drain eye 42 may be defined by a wall having tapered edges. It is envisioned that tip 34 may include one or a plurality of openings.

An expandable member, such as, for example, cuff 50 has a proximal securing portion 52 and a distal securing portion 54. Cuff 50 is disposed along catheter 20 and, overlaps body 22 and tip 34 adjacent a region of fixation, such as, for example, an abutment region 56. Proximal securing portion 52 is disposed about body 22 and secured thereto, as will be discussed. Distal securing portion 54 is disposed about tip 34. Distal securing portion 54 of cuff 50 is bonded over abutment region 56 of body 22 and tip 34, an example of which being described in accordance with a method of manufacture discussed herein. This configuration advantageously provides a more secure and stable tip 34, while removing any visual flash or mismatch from catheter 20. It is envisioned that distal securing portion 54 may be adhesively bonded over a region of fixation between body 22 and tip 34.

Cuff 50 defines an inflation cavity 58 with an outer surface 60 of body 22 that is in fluid communication with inflation lumen 32. Inflation cavity 58 connects with port 33 to facilitate fluid connection with inflation lumen 32. Inflation lumen 32 is configured for fluid flow to inflate cuff 50. Cuff 50 is configured for expansion to retain catheter 20 within the bladder and may include a balloon or similar configuration to facilitate retention. A cross sectional area 62 of central lumen 40 is advantageously greater than a cross sectional area 64 of first lumen 30. This configuration advantageously improves the drainage characteristics of catheter 20. It is contemplated that an expansion device, such as, for example an onion or the like, is disposed within body 22 adjacent cuff 50. It is further contemplated that an inner surface of cuff 50 may include one or plurality of ribs.

Desirably, body 22 and tip 34 are fabricated from a silicone based material having sufficient flexibility and stiffness for disposal within a body cavity. Silicone rubbers or other non-reactive, biologically inert or bio-compatible rubbers, latex, or the like are contemplated. The components of catheter 20 may be fabricated from materials suitable for medical applications, such as, for example, polymerics or metals, such as stainless steel, depending on the particular application and/or preference of a practitioner. Semi-rigid and rigid polymerics are contemplated for fabrication, as well as resilient materials, such as molded medical grade polypropylene. One skilled in the art, however, will realize that other materials and fabrication methods suitable for assembly and manufacture, in accordance with the present disclosure, also would be appropriate.

It is contemplated herein that catheter 20 of the present disclosure may be fabricated and incorporate various materials having different compounds, flexibility and durometer for each respective part, for example, body 22, tip 34 and cuff 50 may be formed from the same or different materials and formed from molding, extrusion or the like.

Referring to FIGS. 6-15, a method of manufacturing a catheter, similar to urological catheter 20 having body 22 and tip 34 is described, in accordance with the principles of the present disclosure. Tip 34 is molded directly onto distal end 26 of body 22, such that tip 34 is connected to body 22 without the use of adhesive.

Figure 7:
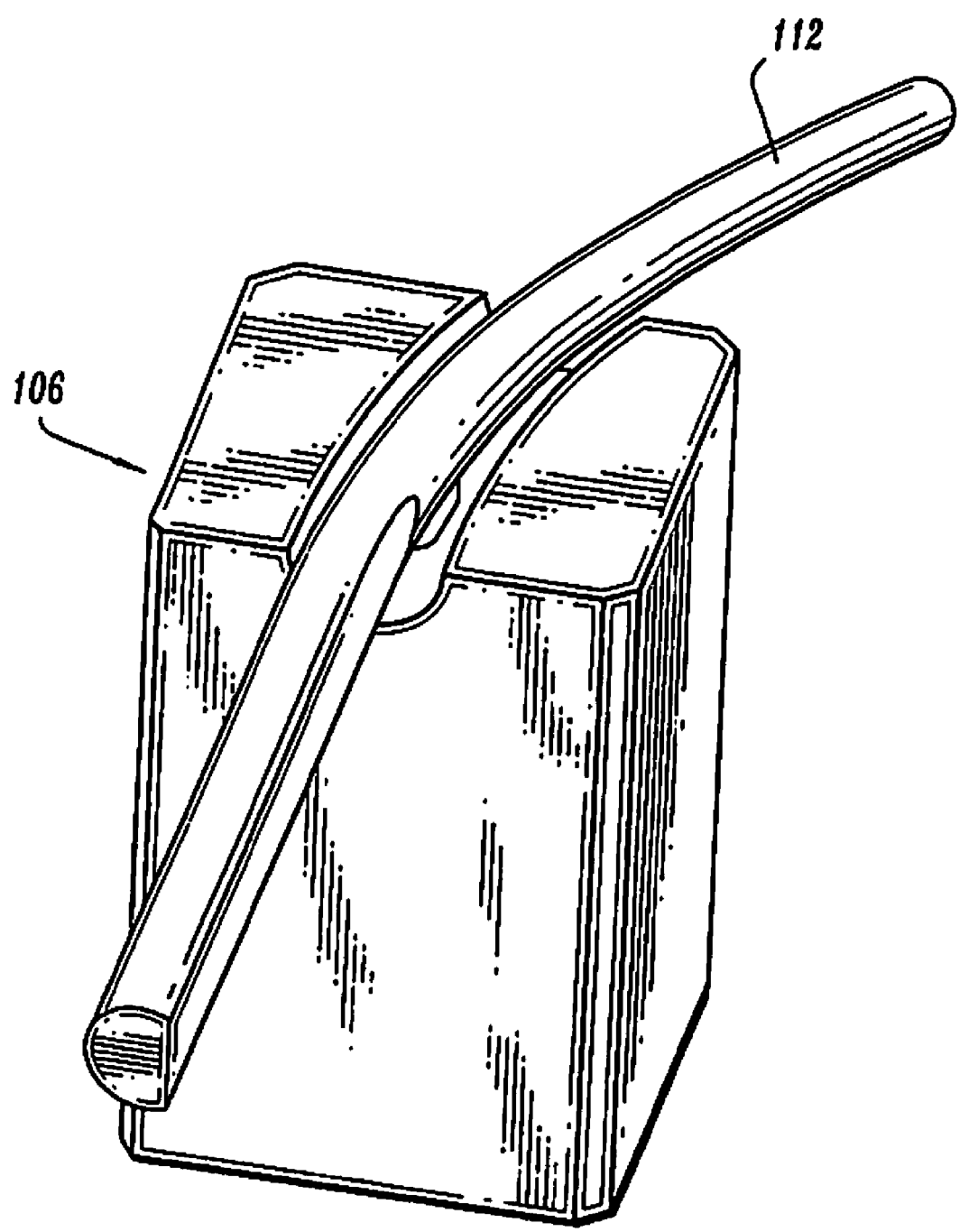
FIG. 7 is a perspective view of a spring block assembly shown in FIG. 6.
Figure 8:
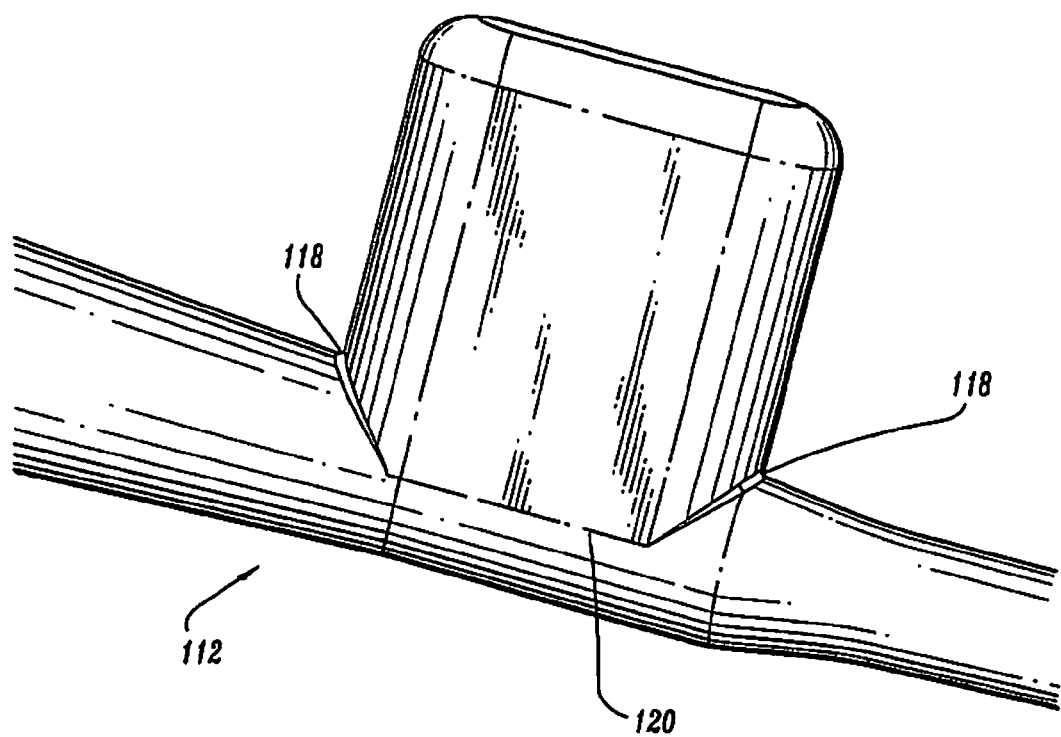
FIG. 8 is a cutaway side perspective view of a pin shown in FIG. 6.

A mold assembly 100 has a mold block 102 that includes a mold cavity 104. Mold assembly 100 has a removable spring block 106, as shown in FIG. 7, that forms a portion of mold cavity 104. Spring block 106 defines a post cavity 108, as shown in FIGS. 11 and 12, that communicates with mold cavity 104. Post cavity 108 defines a predetermined transition, such as, for example, non-perpendicular transition configuration 110 that facilitates formation of radius of curvature R of drain eye 42. A pin 112, as shown in FIGS. 9 and 10, has a core 114 and a post 116 extending therefrom. Post 116 cooperates with non-perpendicular transition configuration 110 to form tip 34. Pin 112 also cooperates with spring block 106 to form drain eye 42. For example, as shown in FIG. 8, surfaces 118 of post 116 cooperate with spring block 106 to form external radii $R_{e1}$ and $R_{e2}$, and internal radii $Ri_1$ and $Ri_2$. Surfaces 120 of post 116 cooperate with non-perpendicular transition configuration 110 to form external radii $R_{e3}$ and $R_{e4}$, and internal radii $R_{i3}$ and $R_{i4}$. It is contemplated that predetermined transition may be variously configured such as, for example perpendicular or disposed at various radial orientations according to the requirements of a particular application.

Figure 14:
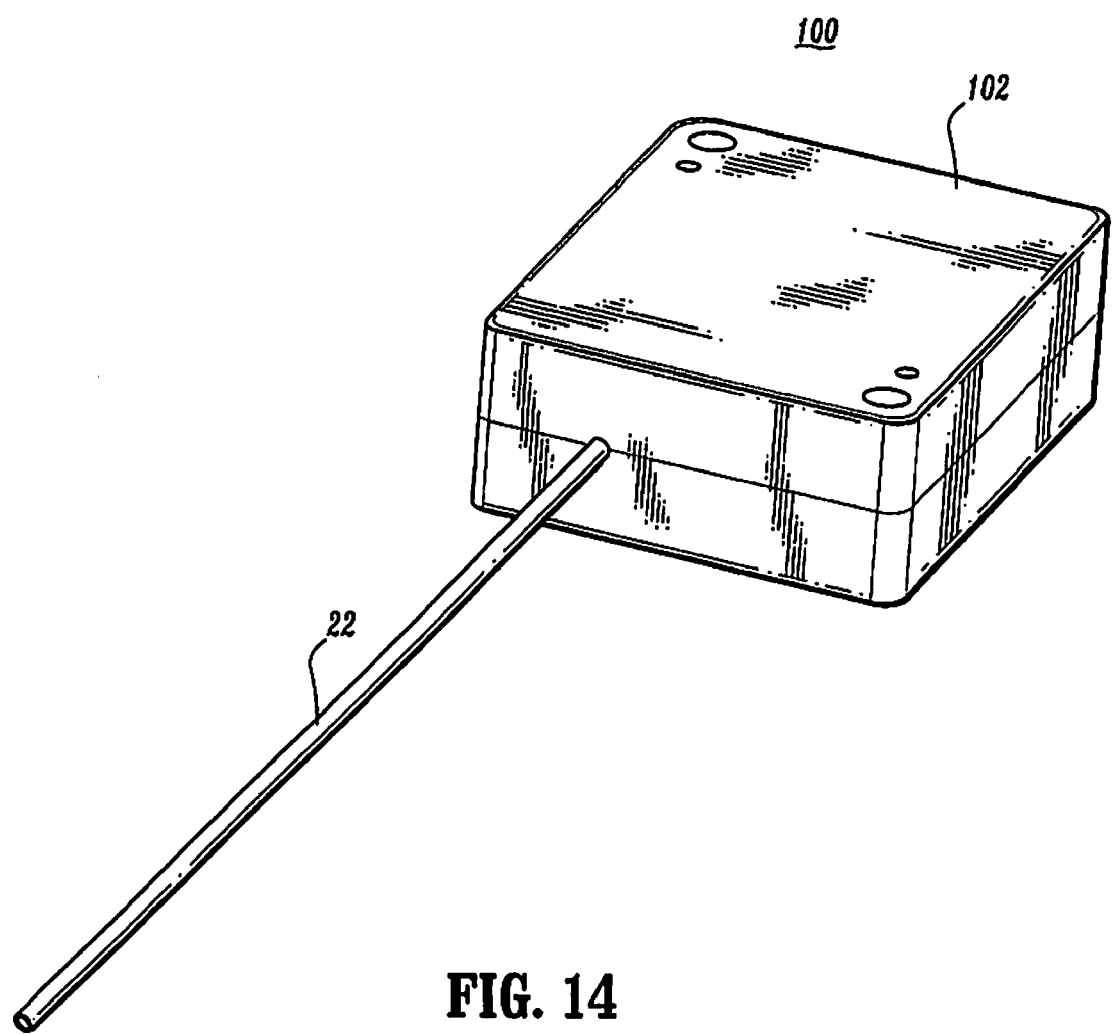
FIG. 14 is a perspective view of the mold assembly, with a catheter disposed therewith.
Figure 15:
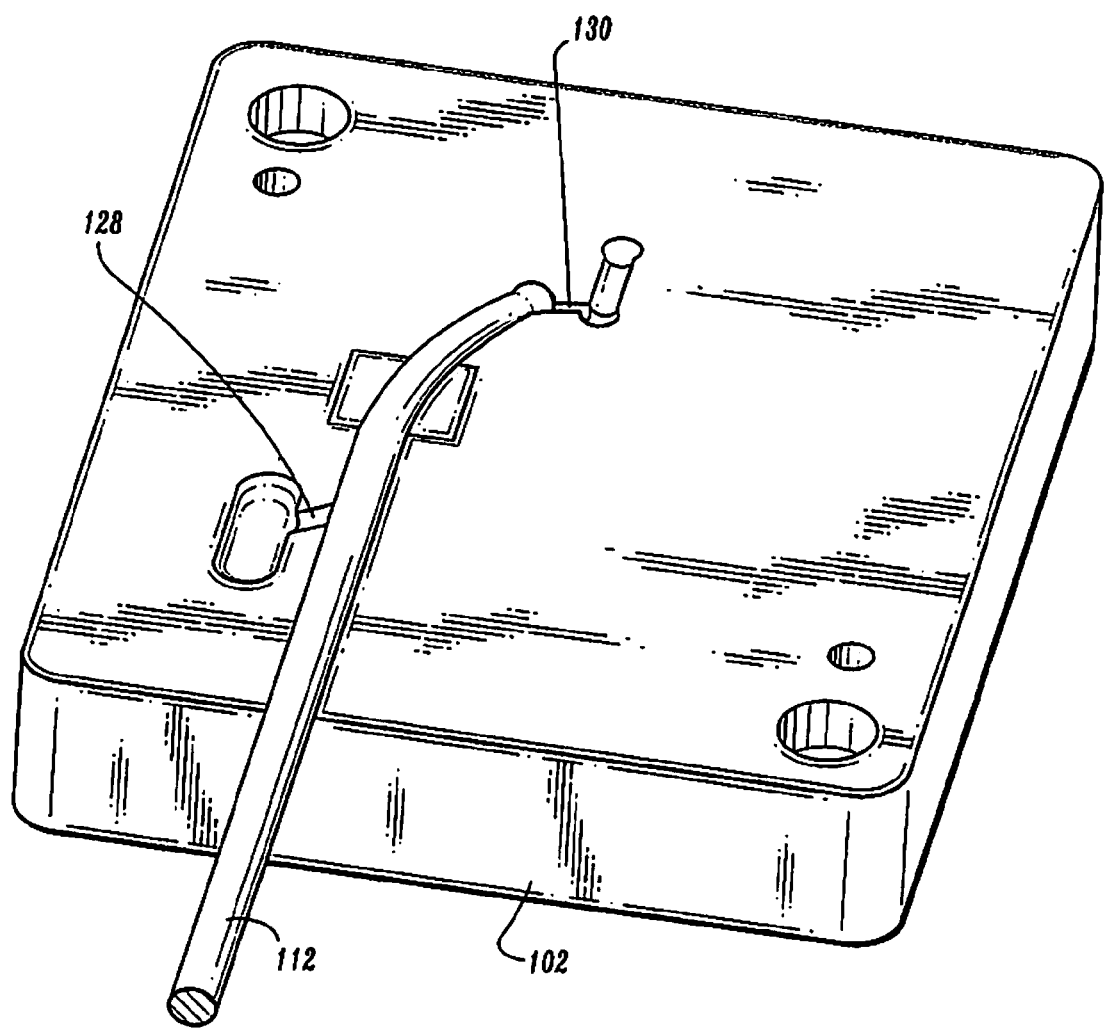
FIG. 15 is a perspective view of the mold assembly and the catheter shown in FIG. 14, with a section removed.

A body 22, similar to that described above, is provided that extends from a proximal end (not shown) to distal end 26. Distal end 26 defines planar face 28 that is disposed along plane y for abutting connection with the tip to be formed. Core 114 of pin 112 is inserted with distal end 26 of body 22 thereby closing a distal end of drainage lumen 30. Distal end 26 of body 22 and pin 112 are disposed with mold cavity 104 such that core 114 of pin 112 is spaced apart from walls 122 of mold cavity 104. Post 116 of pin 112 is disposed with post cavity 108 and extends to engage a wall 124 of post cavity 108, as shown in FIG. 13. Distal end 26 of body 22 is disposed in a channel 126 of mold cavity 104 and body 22 extends out of block 102, as shown in FIG. 14. This configuration facilitates closure of a proximal end of mold cavity 104.

A molten silicone based material is injected into mold cavity 104 via gates 128, 130, as is known, to injection mold tip 34. This molten silicone based material is injected into mold cavity 104 to simultaneously mold tip 34 with distal end 26 of body 22 such that tip 34 defines central lumen 40, and to mold drain eye 42 with tip 34 in relation to the non-perpendicular transition configuration 110. Accordingly, drain eye 42 is defined by a wall 44, which includes external radii $R_{e3}$ and $R_{e4}$ disposed in transition with outer surface 46 of tip 34 and internal radii $R_{i3}$ and $R_{i4}$ disposed in transition with inner surface 48 of tip 34. External radii $R_{e3}$ and $R_{e4}$ have a non-perpendicular profile with outer surface 46 and internal radii $R_{i3}$ and $R_{i4}$ also have a non-perpendicular profile with inner surface 48. External radii $R_{e1}$ and $R_{e2}$, and internal radii $Ri_1$ and $Ri_2$ are also formed simultaneously. Tip 34 is formed with planar face 38 for direct connection and abutment with planar face 28 of body 22. Cylindrical head 35 is also formed. Other molten materials are contemplated for injection molding.

After tip 34 has sufficiently cured, spring block 106, having pin 112 disposed therewith, and body 22 are removed from mold cavity 104. Body 22, having tip 34 molded thereto, and pin 112 disposed therein, are removed from spring block 106. Pin 112 is removed from tip 34 through drain eye 42. Core 114 of pin 112 is disposed in central lumen 40 and post 116 extends through drain eye 42. Tip 34 is flexed slightly to manipulate the distal end of tip 34 over the distal end of pin 112. The remaining portion of core 114 is drawn through drain eye 42 from central lumen 40 and consequently out of tip 34. A source of pressurized gas may be connected to body 22 to blow catheter 20 off pin 112. Thus, tip 34 is advantageously directly molded to body 22 adjacent an abutment region 56 of catheter 20 while forming central lumen 40 and drainage eye 42.

Cuff 50 is mounted about body 22 and tip 34. Proximal securing portion 52 of cuff 50 is bonded to body 22 at a zone 132 (FIG. 2) adjacent distal end 26. Distal securing portion 54 of cuff 50 is bonded over abutment region 56 of body 22 and tip 34. Cuff 50 overlaps body 22 and tip 34 to form inflation cavity 58 with outer surface 60 of body 22. Cuff 50 is connected with port 33 to establish communication with inflation lumen 32. Proximal securing portion 52 and distal securing portion 54 may be adhesively bonded to body 22 and tip 34, or attached alternatively by clips, staples or other bonding techniques.

Figure 16:
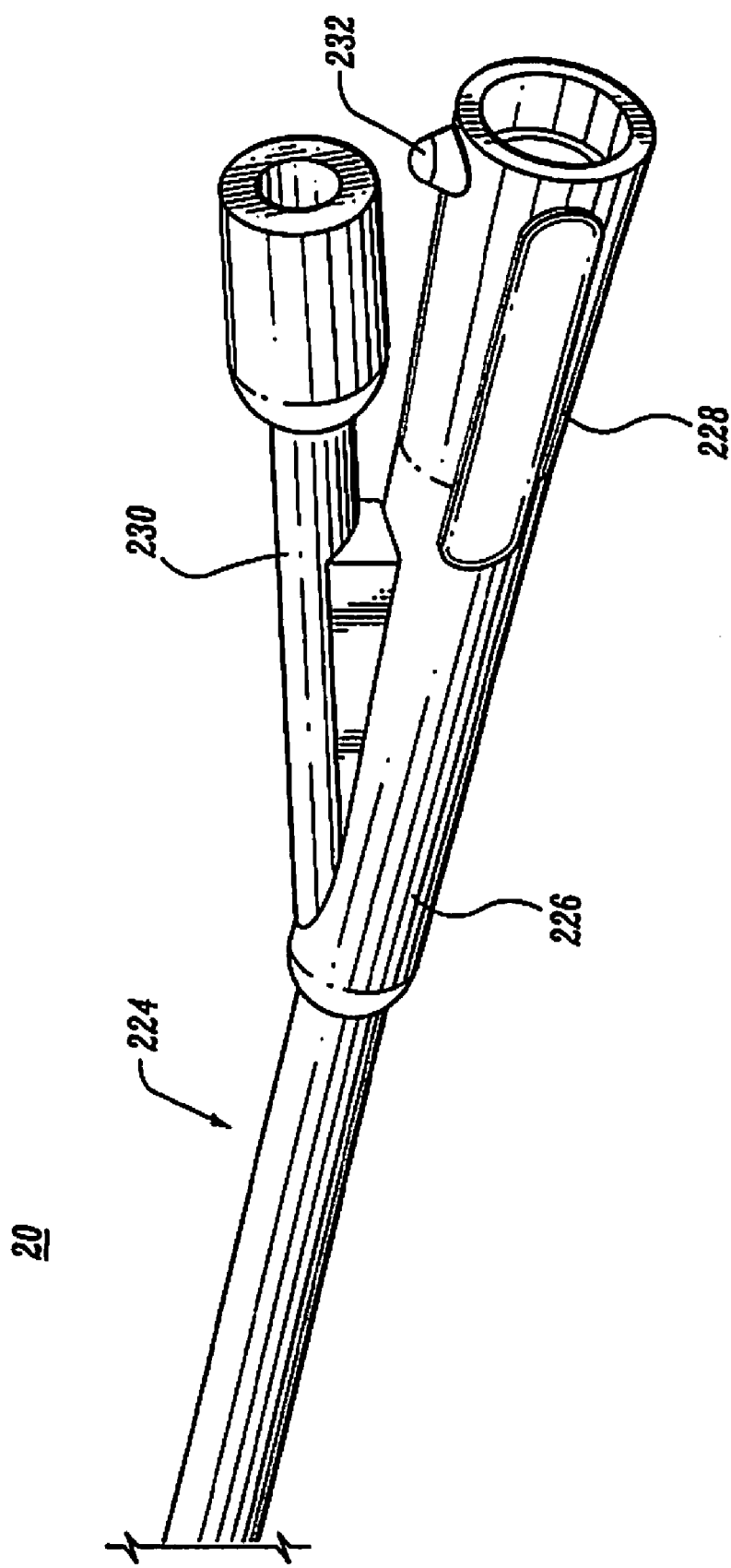
FIG. 16 is a cutaway perspective view of a proximal end of an alternate embodiment of the urology catheter shown in FIG. 1.
Figure 17:
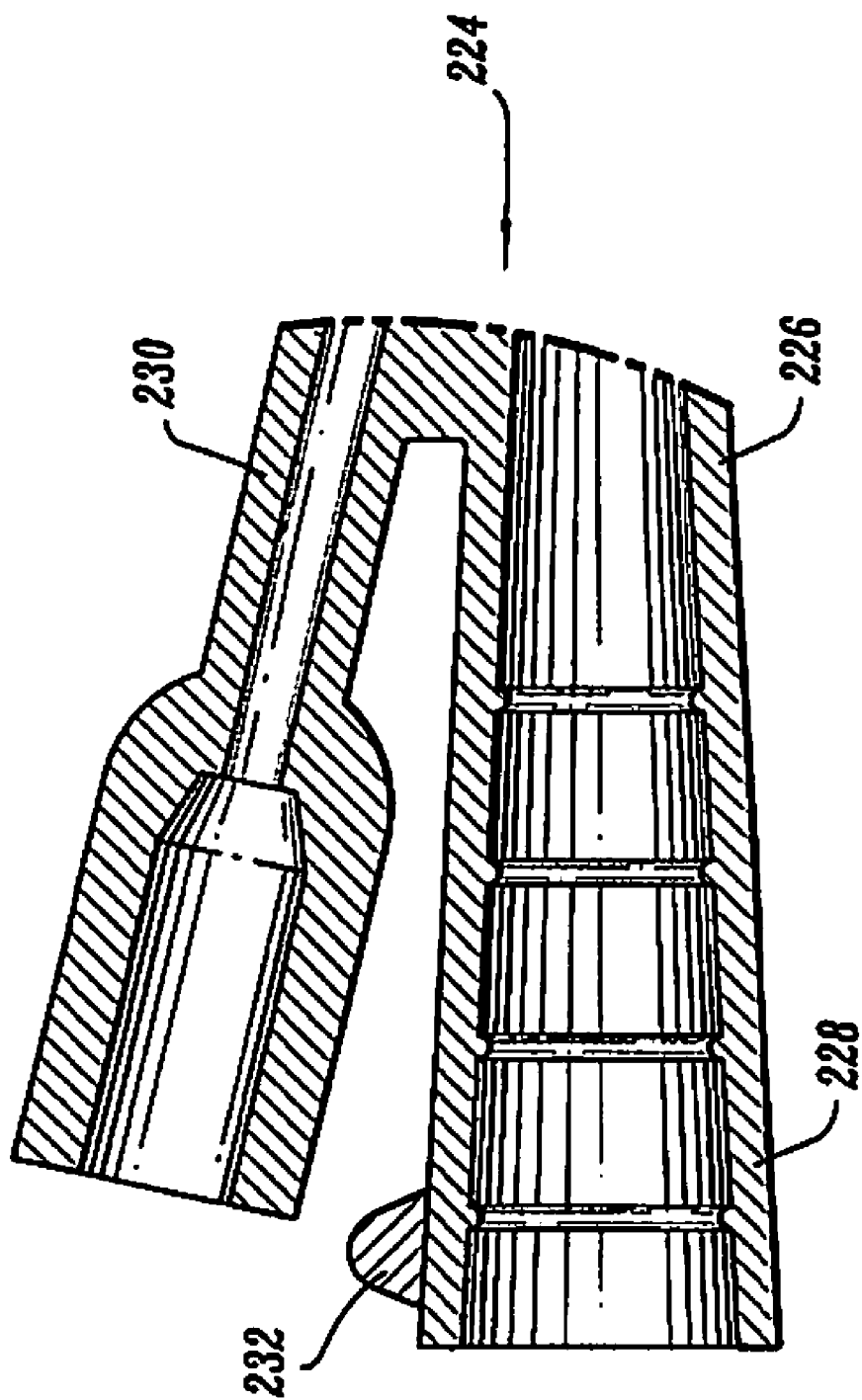
FIG. 17 is a cutaway side cross-sectional view of the proximal end of the urology catheter shown in FIG. 16.

Referring to FIGS. 16 and 17, an alternate embodiment of catheter 20, similar to that described above, is shown. Catheter 20 includes a proximal end 224 that is attached to a connector 226. Connector 226 includes an adapter 228 that communicates with drainage lumen 30. Adapter 228 is configured for connection to a drainage receptacle (not shown) for urine collection. Connector 226 also includes an arm 230 that communicates with inflation lumen 32. Arm 230 is configured for connection to a inflation fluid/gas source.

Connector 226 includes a projection, such as, for example, bump 232 that is configured to provide visual indicia and tactile indicia of the orientation of tip 34 when disposed with the subject. For example, catheter 20 can be rotated to orient tip 34 through a body cavity during use. A practitioner manipulating catheter 20 can determine orientation of tip 34 according to the tactile feel provided by bump 232. Alternatively, body 22 may be fabricated from a material having a first indicia of color, and bump 232 may be fabricated from a material having a second indicia of color. In use, the practitioner can determine orientation of tip 34 according to orientation and corresponding visual representation provided by bump 232 due to the distinction in color of body 22 and the color of bump 232. It is contemplated that proximal end 224 and/or bump 232 may be fabricated in an injection molding step separate from the injection molding fabrication of body 22 and tip 34 discussed above with regard to FIGS. 6-15.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method of manufacturing a catheter having a body and a tip, the method comprising the steps of:
   providing a mold that defines a mold cavity and a post cavity that communicates with the mold cavity, the post cavity defining a predetermined transition configuration;
   providing a pin having a post extending therefrom, the post cooperating with the predetermined transition configuration of the post cavity to form the tip;
   inserting the pin with a distal end of the body;
   disposing the distal end of the body and the pin into the mold cavity such that the post is disposed with the post cavity and extends to engage a wall of the post cavity;
   injecting a material into the mold cavity to simultaneously mold the tip with the distal end of the body, and to mold a lateral opening with the tip in relation to the predetermined transition configuration such that the lateral opening is defined by a wall including an external radius disposed in transition with an outer surface of the tip and an internal radius disposed in transition with an inner surface of the tip, the external radius having a non-perpendicular profile with the outer surface of the tip;
   removing the body and the pin from the mold cavity; and
   removing the pin from the catheter through the lateral opening.

2. A method as recited in claim 1, wherein the mold includes a removable block that forms a portion of the mold cavity and defines the post cavity.

3. A method as recited in claim 2, wherein the step of removing the body and the pin from the mold cavity further includes removing the block, having the pin disposed therewith, from the mold.

4. A method as recited in claim 1, wherein the step of disposing includes disposing the pin with the mold cavity such that the pin is spaced apart from walls of the mold cavity.

5. A method as recited in claim 1, wherein the material includes a silicone based rubber.

6. A method as recited in claim 1, wherein the step of injecting includes molding a tip that defines a central lumen in communication with the lateral opening.

7. A method as recited in claim 1, further comprising the step of mounting an expandable member about the body and the tip.

8. A method of manufacturing a catheter having a body and a tip, the method comprising the steps of:
   providing a mold assembly that includes a mold cavity, the mold assembly having a removable spring block that forms a portion of the mold cavity and defines a post cavity that communicates with the mold cavity, the post cavity defining a non-perpendicular transition configuration;
   providing a pin having a core and a post extending therefrom, the post cooperating with the non-perpendicular transition configuration to form the tip;
   inserting the core with a distal end of the body;
   disposing the distal end of the body and the pin with the mold cavity such that the core is spaced apart from walls of the mold cavity and the post is disposed with the post cavity and extends to engage a wall of the post cavity;
   injecting a silicone based material into the mold cavity to simultaneously mold the tip with the distal end of the body such that the tip defines a central lumen, and to mold a lateral opening with the tip in relation to the non-perpendicular transition configuration such that the lateral opening is defined by a wall including an external radius disposed in transition with an outer surface of the tip and an internal radius disposed in transition with an inner surface of the tip, the external radius having a non-perpendicular profile with the outer surface of the tip and the internal radius having a non-perpendicular profile with the inner surface of the tip;
   removing the body and the spring block, having the pin disposed therewith, from the mold cavity;
   removing the pin from the tip through the lateral opening; and
   mounting an expandable sleeve about the body and the tip.

* * * * *